(12) United States Patent
Torres, Jr.

(10) Patent No.: US 10,857,024 B2
(45) Date of Patent: Dec. 8, 2020

(54) POCKETED ARM SLING ASSEMBLY

(71) Applicant: Daniel M. Torres, Jr., Menifee, CA (US)

(72) Inventor: Daniel M. Torres, Jr., Menifee, CA (US)

( * ) Notice: Subject to any disclaimer, the term of this patent is extended or adjusted under 35 U.S.C. 154(b) by 366 days.

(21) Appl. No.: 15/825,847

(22) Filed: Nov. 29, 2017

(65) Prior Publication Data

US 2019/0159924 A1    May 30, 2019

(51) Int. Cl.
| | |
|---|---|
| *A61F 5/40* | (2006.01) |
| *A61F 5/37* | (2006.01) |
| *A45F 3/02* | (2006.01) |
| *A45C 9/00* | (2006.01) |
| *A45F 5/00* | (2006.01) |

(52) U.S. Cl.
CPC .............. *A61F 5/3738* (2013.01); *A45C 9/00* (2013.01); *A45F 3/02* (2013.01); *A45F 5/00* (2013.01); *A45F 2200/0516* (2013.01); *A45F 2200/0525* (2013.01); *A45F 2200/0558* (2013.01); *A45F 2200/0575* (2013.01)

(58) Field of Classification Search
CPC ...... A61F 5/3738; A61F 5/3753; A61F 5/373; A61F 5/3723; A61F 5/3746; A45C 9/00; A45F 3/02; A45F 2200/0575; A45F 2200/0558; A45F 2200/0525; A45F 2200/0516
See application file for complete search history.

(56) References Cited

U.S. PATENT DOCUMENTS

| | | | |
|---|---|---|---|
| 4,232,664 A * | 11/1980 | Blatt | A61F 5/3738 602/4 |
| 4,285,337 A | 8/1981 | Cosentino | |
| 4,526,164 A | 7/1985 | Bihl | |
| 4,622,961 A | 11/1986 | Christensen | |
| 4,625,719 A | 12/1986 | Chambers | |
| 4,759,353 A * | 7/1988 | Melendez | A61F 5/3738 602/4 |
| 5,072,455 A * | 12/1991 | St. Ours | A41D 13/0055 2/81 |
| 5,464,383 A * | 11/1995 | Padden | A61F 5/3753 128/878 |
| D577,123 S | 9/2008 | True | |
| 7,841,997 B1 * | 11/2010 | Heller | A61F 5/3738 602/4 |

(Continued)

FOREIGN PATENT DOCUMENTS

WO    WO2013032449    3/2013

*Primary Examiner* — Rachael E Bredefeld
*Assistant Examiner* — Camtu T Nguyen

(57) ABSTRACT

A pocketed arm sling assembly for stowing personal items of a user includes a sleeve that is configured to insert a forearm of the user. A first strap is coupled to and extends between a first end and a second end of the sleeve to define a loop. Each of a plurality of panels is coupled by a lower edge and opposing side edges to a respective opposing side of the sleeve to define a pocket. An opening is defined by an upper edge of the panel and the sleeve. The loop is configured to position around a neck of the user to couple the sleeve to the user to support the forearm that is positioned in the sleeve. The pockets are positioned on the sleeve so that each pocket is positioned to stow a respective personal item of the user.

1 Claim, 4 Drawing Sheets

(56) References Cited

U.S. PATENT DOCUMENTS

2008/0015479 A1 1/2008 Soscia
2011/0219522 A1* 9/2011 Petitt ..................... A42B 1/245
2/422

* cited by examiner

POCKETED ARM SLING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to sling assemblies and more particularly pertains to a new sling assembly for stowing personal items of a user.

BRIEF SUMMARY OF THE INVENTION

An embodiment of the disclosure meets the needs presented above by generally comprising a sleeve that is configured to insert a forearm of a user. A first strap is coupled to and extends between a first end and a second end of the sleeve to define a loop. Each of a plurality of panels is coupled by a lower edge and opposing side edges to a respective opposing side of the sleeve to define a pocket. An opening is defined by an upper edge of the panel and the sleeve. The loop is configured to position around a neck of the user to couple the sleeve to the user to support the forearm that is positioned in the sleeve. The pockets are positioned on the sleeve so that each pocket is positioned to stow a respective personal item of the user.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
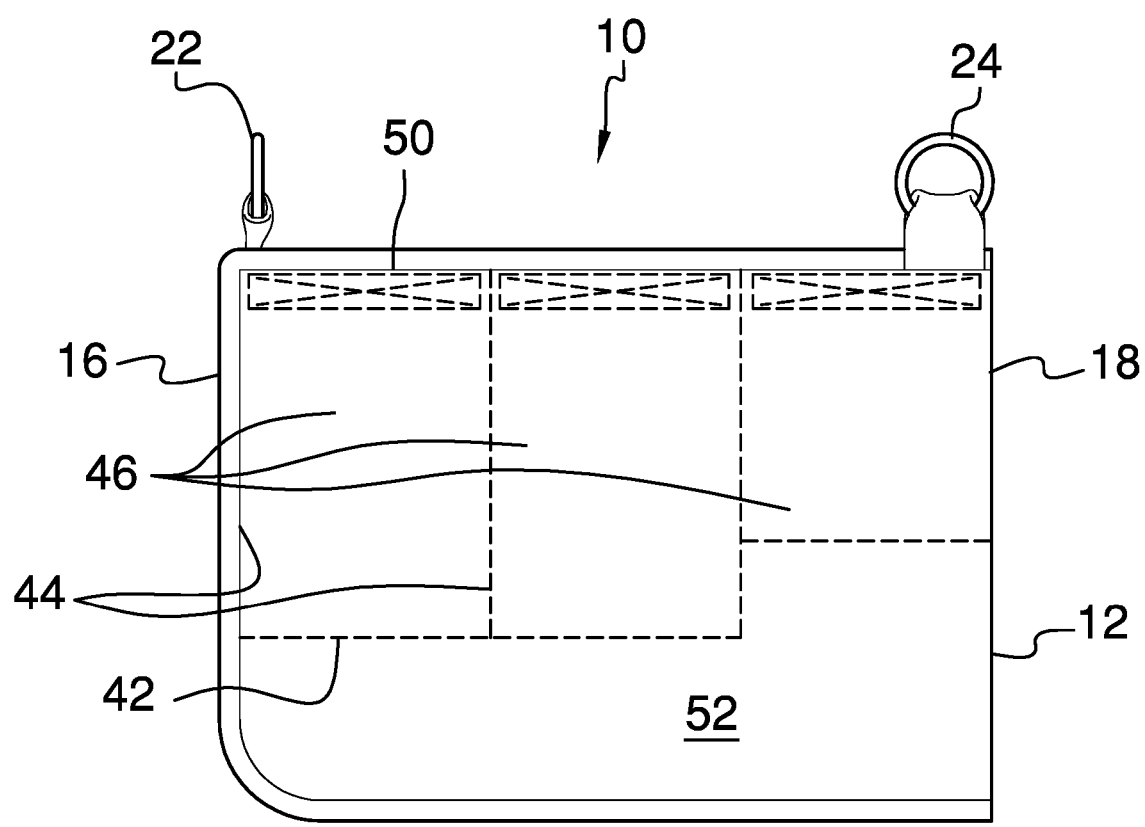
FIG. 1 is a side view of a pocketed arm sling assembly according to an embodiment of the disclosure.
Figure 2:
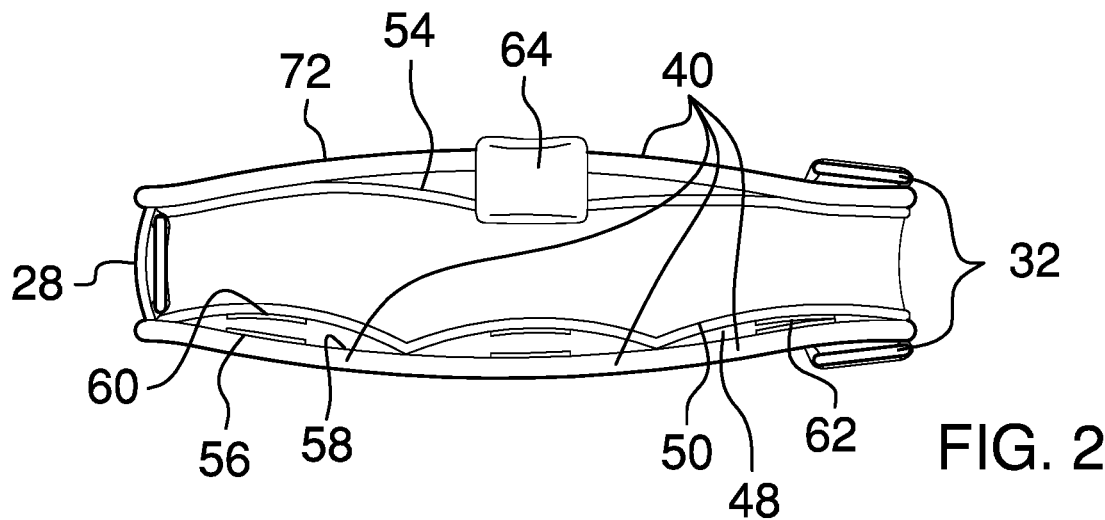
FIG. 2 is a top view of an embodiment of the disclosure.
Figure 3:
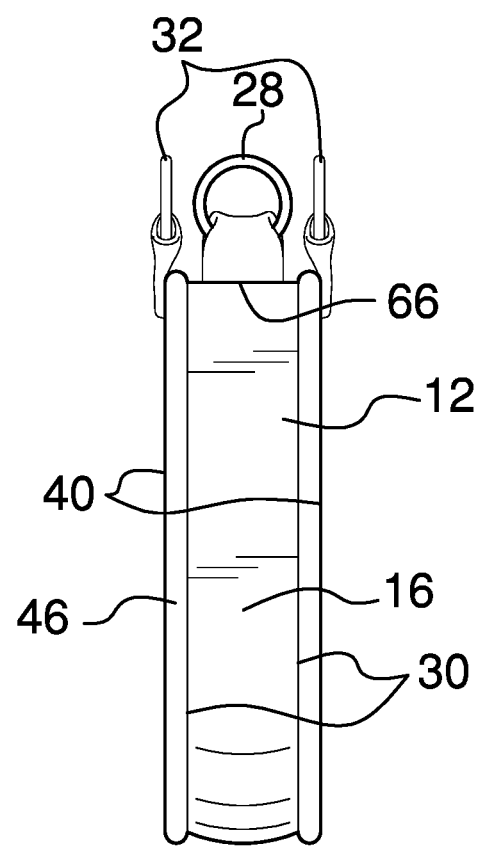
FIG. 3 is an end view of an embodiment of the disclosure.
Figure 4:
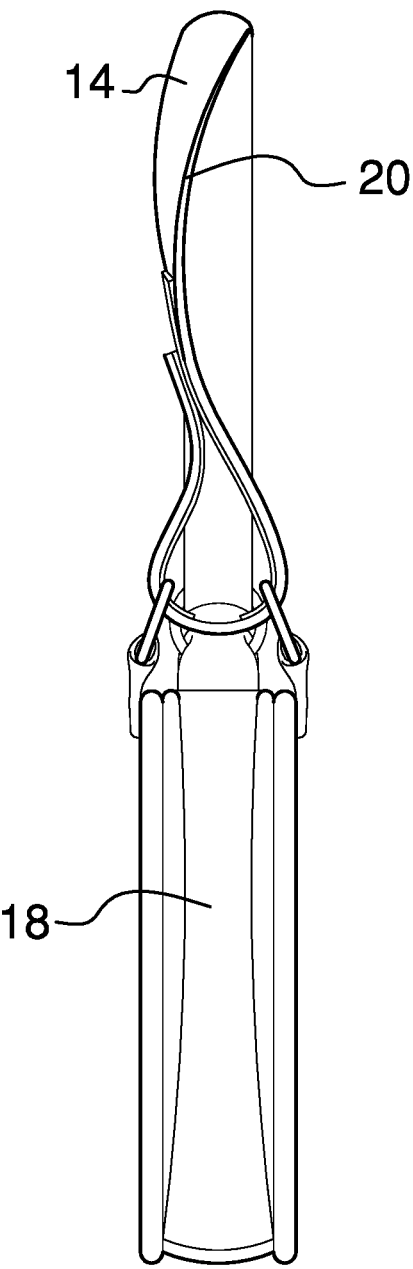
FIG. 4 is an end view of an embodiment of the disclosure.
Figure 5:
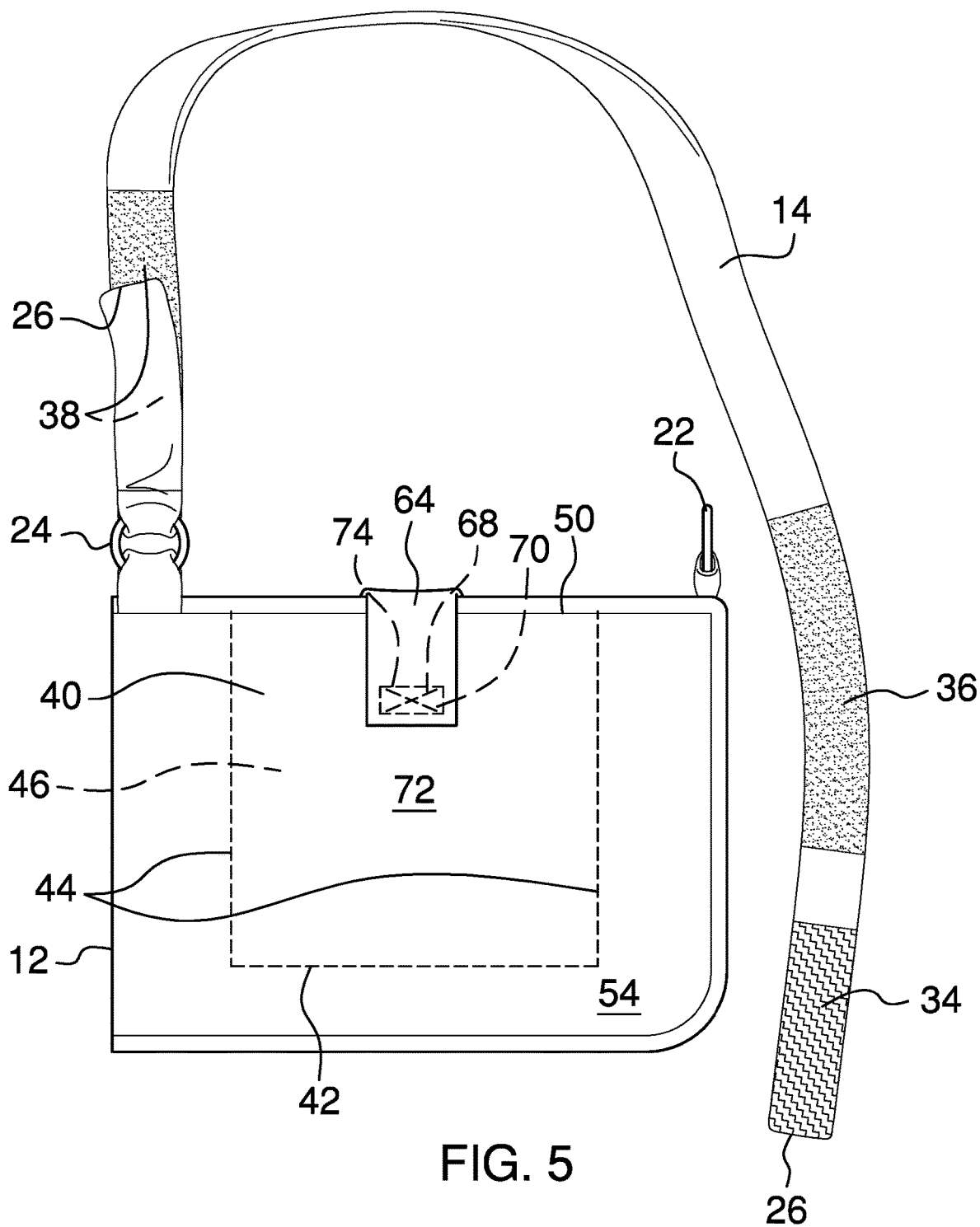
FIG. 5 is a side view of an embodiment of the disclosure.

With reference now to the drawings, and in particular to FIGS. 1 through 6 thereof, a new sling assembly embodying the principles and concepts of an embodiment of the disclosure and generally designated by the reference numeral 10 will be described.

As best illustrated in FIGS. 1 through 6, the pocketed arm sling assembly 10 generally comprises a sleeve 12 that is configured to insert a forearm of a user. The sleeve 12 is sized to extend from proximate to an elbow to proximate to a wrist of the user. The sleeve 12 is sized such that a top 66 of the sleeve 12 extends to proximate to a midpoint of an upper arm of the user when the forearm is perpendicular to the upper arm.

A first strap 14 is coupled to and extends between a first end 16 and a second end 18 of the sleeve 12 and defines a loop 20. The loop 20 is configured to position around a neck of the user to couple the sleeve 12 to the user to support the forearm that is positioned in the sleeve 12. The first strap 14 is selectively length-adjustable and reversibly couplable to the sleeve 12 so that the sleeve 12 is selectively positionable relative to the neck of the user.

A first connector 22 is coupled to the first end 16 of the sleeve 12. second connector 24 is coupled to the second end 18 of the sleeve 12. The first connector 22 and the second connector 24 each are configured to selectively couple to a respective opposing end 26 of the first strap 14 to couple the sleeve 12 to the first strap 14 and define the loop 20. The first connector 22 comprises a first ring 28. The first ring 28 is positioned perpendicularly to opposing sides 30 of the sleeve 12. The second connector 24 comprises a pair of second rings 32. Each second ring 32 extends substantially coplanarly from a respective opposing side 30 of the sleeve 12.

Each of a pair of first fasteners 34 is coupled to the first strap 14 proximate to a respective opposing end 26 of the first strap 14. Each of a pair of second fasteners 36 is coupled to the first strap 14 adjacent to an associated first fastener 34. The second fasteners 36 are complementary to the first fasteners 34. The opposing ends 26 of the first strap 14 are positioned to insert singly through the first ring 28 and the pair of second rings 32 to position the second fastener 36 to couple to the associated first fastener 34 to couple the strap to the sleeve 12 and define the loop 20. Each second fastener 36 and the associated first fastener 34 comprise a first hook and loop fastener 38 or the like.

Figure 6:
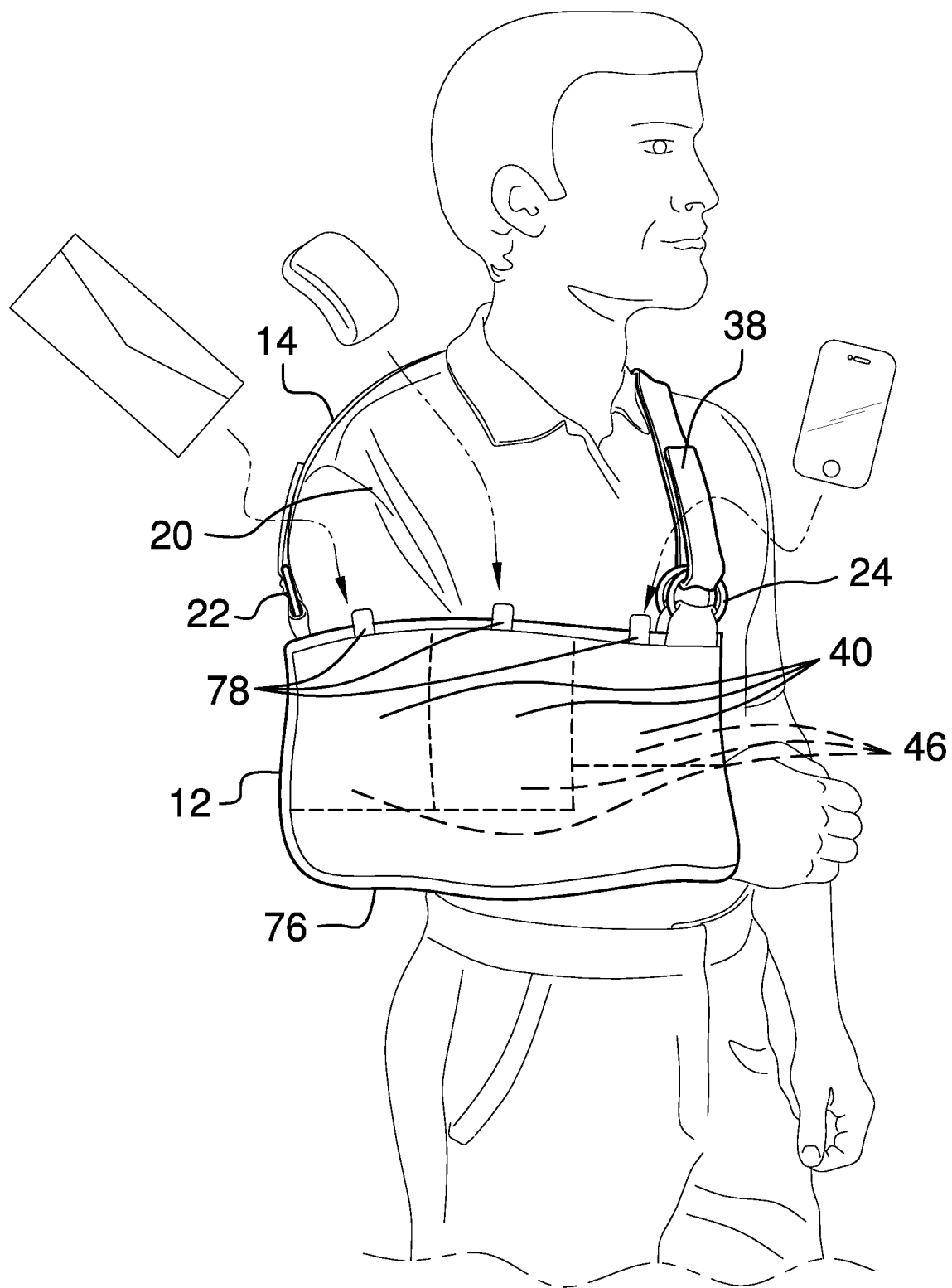
FIG. 6 is an in-use view of an embodiment of the disclosure.

Each of a plurality of panels 40 is coupled by a lower edge 42 and opposing side edges 44 to a respective opposing side 30 of the sleeve 12 to define a pocket 46. An opening 48 is defined by an upper edge 50 of the panel 40 and the sleeve 12. Each pocket 46 is positioned to stow a respective personal item of the user, such as a wallet, a cellphone, keys, and a tablet computer. The plurality of panels 40 comprises three panels 40 that are coupled to a first face 52 of the sleeve 12, which are configured for positioning the personal items, such as the wallet, the cellphone, and the keys. As shown in FIG. 1, the three panels extend from the top 66 of the sleeve 12 partway to a bottom 76 of the sleeve 12. As shown in FIG. 6, the three panels extend from the top 66 of the sleeve 12 all the way to the bottom 76 of the sleeve 12. The plurality of panels 40 also comprises one panel 40 that is coupled to a second face 54 of the sleeve 12, which is configured for positioning the personal item, such as the tablet computer.

Each of a plurality of third fasteners 56 is coupled to an interior surface 58 proximate to the upper edge 50 of a respective panel 40. A plurality of fourth fasteners 60 is coupled to the first face 52 of the sleeve 12. The fourth fasteners 60 are complementary to the third fasteners 56. Each fourth fastener 60 is positioned to selectively couple to an associated third fastener 56 to couple the respective panel 40 to the sleeve 12 to close the opening 48 of the pocket 46 that is defined by the respective panel 40 that is positioned on the first face 52 of the sleeve 12. Each fourth fastener 60 and the associated third fastener 56 comprise a second hook and loop fastener 62 or the like.

As shown in FIG. 6, each of a plurality of tabs 78 is coupled to the upper edge 50 of a respective panel 40 that positioned on the first face 52 of the sleeve 12. A respective tab 78 is configured to be grasped in digits of a hand of the user to separate an associated second hook and loop fastener 62 to open an associated pocket 46.

A second strap 64 is coupled to the top 66 of the sleeve 12 substantially equally distant from the first end 16 and the second end 18 of the sleeve 12. A fifth fastener 68 is coupled to the second strap 64 distal from the sleeve 12. A sixth fastener 70 is coupled to an exterior surface 72 of the panel 40 that is positioned on the second face 54 of the sleeve 12. The sixth fastener 70 is complementary to the fifth fastener 68. The fifth fastener 68 is positioned to selectively couple to the sixth fastener 70 to close the opening 48 of the pocket 46 that is defined by the panel 40 that is positioned on the second face 54 of the sleeve 12. The fifth fastener 68 and the sixth fastener 70 comprise a third hook and loop fastener 74 or the like.

In use, the opposing ends 26 of the first strap 14 are positioned to insert singly through the first ring 28 and the pair of second rings 32. The second fastener 36 is positioned to couple to the associated first fastener 34 to couple the strap to the sleeve 12 so that first strap 14 is selectively length-adjustable. The loop 20 is configured to position around the neck of the user to couple the sleeve 12 to the user to support the forearm that is positioned in the sleeve 12. Each pocket 46 is positioned to stow the respective personal item of the user. Each fourth fastener 60 is positioned to selectively couple to the associated third fastener 56 to couple the respective panel 40 to the sleeve 12 to close the opening 48 of the pocket 46 that is defined by the respective panel 40 that is positioned on the first face 52 of the sleeve 12. The fifth fastener 68 is positioned to selectively couple to the sixth fastener 70 to close the opening 48 of the pocket 46 that is defined by the panel 40 that is positioned on the second face 54 of the sleeve 12.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A pocketed arm sling assembly comprising:
    a sleeve configured for inserting a forearm of a user, said sleeve being sized to extend from proximate to an elbow to proximate to a wrist of the user, said sleeve being sized such that a top of said sleeve extends to proximate to a midpoint of an upper arm of the user when the forearm is perpendicular to the upper arm;
    a first strap coupled to and extending between a first end and a second end of said sleeve defining a loop, wherein said first strap is positioned on said sleeve such that said loop is configured for positioning around a neck of the user for coupling said sleeve to the user for supporting the forearm positioned in said sleeve, said first strap being selectively length-adjustable such that said sleeve is selectively positionable relative to the neck of the user, said first strap being reversibly couplable to said sleeve;
    a first connector coupled to said first end of said sleeve;
    a second connector coupled to said second end of said sleeve, said first connector and said second connector each being configured for selectively coupling to a respective opposing end of said first strap, wherein said first connector and said second connector are positioned on said sleeve such that said first connector and said second connector are positioned for coupling said sleeve to said first strap defining said loop, said first connector comprising a first ring, said first ring being positioned perpendicularly to said opposing sides of said sleeve, said second connector comprising a pair of second rings, each said second ring extending substantially coplanarly from a respective opposing side of said sleeve;
    a pair of first fasteners, each said first fastener being coupled to said first strap proximate to a respective opposing end of said first strap;
    a pair of second fasteners, said second fasteners being complementary to said first fasteners, each said second fastener being coupled to said first strap adjacent to an associated said first fastener, wherein said second fasteners are positioned on said first strap such that said opposing ends of said first strap are positioned for inserting singly through said first ring and said pair of second rings positioning said second fastener for coupling to said associated said first fastener for coupling said first strap to said sleeve defining said loop, each said second fastener and said associated said first fastener comprising a first hook and loop fastener;

a plurality of panels, each said panel being coupled by a lower edge and opposing side edges to a respective said opposing side of said sleeve defining a pocket having an opening defined by an upper edge of said panel and said sleeve, wherein said pockets are positioned on said sleeve such that each said pocket is positioned for stowing a respective personal item of the user, said plurality of panels comprising three said panels coupled to a first face of said sleeve and one said panel coupled to a second face of said sleeve;

a plurality of third fasteners, each said third fastener being coupled to an interior surface proximate to said upper edge of a respective said panel;

a plurality of fourth fasteners coupled to said first face of said sleeve, said fourth fasteners being complementary to said third fasteners, wherein said fourth fasteners are positioned on said sleeve such that each said fourth fastener is positioned for selectively coupling to an associated said third fastener for coupling said respective said panel to said sleeve for closing said opening of said pocket defined by said respective said panel positioned on said first face of said sleeve, each said fourth fastener and said associated said third fastener comprising a second hook and loop fastener;

a plurality of tabs, each said tab being coupled to said upper edge of said respective said panel positioned on said first face of said sleeve such that said tab is configured for grasping in digits of a hand of the user for separating an associated said second hook and loop fastener for opening an associated said pocket;

a second strap coupled to said top of said sleeve substantially equally distant from said first end and said second end of said sleeve;

a fifth fastener coupled to said second strap distal from said sleeve;

a sixth fastener coupled to an exterior surface of said panel positioned on said second face of said sleeve, said sixth fastener being complementary to said fifth fastener, wherein said fifth fastener is positioned on said second strap such that said fifth fastener is positioned for selectively coupling to said sixth fastener for closing said opening of said pocket defined by said panel positioned on said second face of said sleeve, said fifth fastener and said sixth fastener comprising a third hook and loop fastener; and wherein said second fasteners are positioned on said first strap such that said opposing ends of said first strap are positioned for inserting singly through said first ring and said pair of second rings positioning said second fastener for coupling to said associated said first fastener for coupling said first strap to said sleeve defining said loop such that said loop is configured for positioning around the neck of the user for coupling said sleeve to the user for supporting the forearm positioned in said sleeve and such that said first strap is selectively length-adjustable, wherein said pockets are positioned on said sleeve such that each said pocket is positioned for stowing the respective personal item of the user, wherein said fourth fasteners are positioned on said sleeve such that each said fourth fastener is positioned for selectively coupling to said associated said third fastener for coupling said respective said panel to said sleeve for closing said opening of said pocket defined by said respective said panel positioned on said first face of said sleeve, wherein said fifth fastener is positioned on said second strap such that said fifth fastener is positioned for selectively coupling to said sixth fastener for closing said opening of said pocket defined by said panel positioned on said second face of said sleeve.

* * * * *